(12) United States Patent
Kramer et al.

(10) Patent No.: US 11,952,493 B2
(45) Date of Patent: *Apr. 9, 2024

(54) MOISTURE-CURING POLYURETHANE COMPOSITION CONTAINING OXAZOLIDINE

(71) Applicant: SIKA TECHNOLOGY AG, Baar (CH)

(72) Inventors: Andreas Kramer, Zürich (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 527 days.

This patent is subject to a terminal disclaimer.

(21) Appl. No.: 17/294,518

(22) PCT Filed: Dec. 12, 2019

(86) PCT No.: PCT/EP2019/084940
§ 371 (c)(1),
(2) Date: May 17, 2021

(87) PCT Pub. No.: WO2020/126841
PCT Pub. Date: Jun. 25, 2020

(65) Prior Publication Data
US 2022/0025176 A1  Jan. 27, 2022

(30) Foreign Application Priority Data

Dec. 17, 2018 (EP) .................. 18213019

(51) Int. Cl.
| | | |
|---|---|---|
| C08L 75/08 | (2006.01) |
| C08G 18/12 | (2006.01) |
| C08G 18/28 | (2006.01) |
| C08G 18/30 | (2006.01) |
| C08G 18/48 | (2006.01) |
| C08G 18/50 | (2006.01) |
| C08G 18/76 | (2006.01) |
| C08G 18/78 | (2006.01) |
| C08L 75/04 | (2006.01) |

(52) U.S. Cl.
CPC ............ *C08L 75/08* (2013.01); *C08G 18/12* (2013.01); *C08G 18/2865* (2013.01); *C08G 18/307* (2013.01); *C08G 18/4812* (2013.01); *C08G 18/4825* (2013.01); *C08G 18/4829* (2013.01); *C08G 18/5048* (2013.01); *C08G 18/7657* (2013.01); *C08G 18/7862* (2013.01); *C08L 75/04* (2013.01); *C08G 2150/00* (2013.01); *C08G 2170/00* (2013.01); *C08G 2190/00* (2013.01)

(58) Field of Classification Search
CPC ...... C08L 75/04; C08L 75/08; C08G 18/2865
See application file for complete search history.

(56) References Cited

U.S. PATENT DOCUMENTS

| 6,255,433 B1 | 7/2001 | Kuroda et al. | |
| 11,242,428 B2 * | 2/2022 | Burckhardt | C08G 18/7664 |
| 11,535,694 B2 * | 12/2022 | Burckhardt | C08G 18/3296 |

FOREIGN PATENT DOCUMENTS

| JP | 2010-024285 A | 2/2010 | |
| WO | WO-2017108829 A1 * | 6/2017 | ........... C07C 251/24 |

OTHER PUBLICATIONS

Feb. 27, 2020 International Search Report issued in International Patent Application No. PCT/EP2019/084940.
Jun. 16, 2021 International Preliminary Report on Patentability issued in International Patent Application No. PCT/EP2019/084940.

* cited by examiner

*Primary Examiner* — Vickey Nerangis
(74) *Attorney, Agent, or Firm* — Oliff PLC

(57) ABSTRACT

A polyurethane composition, which contains at least one isocyanate-group-containing polymer, obtained from the reaction of at least one polyol with at least one diisocyanate, and at least one oxazolidine of the formula (I). The polyurethane composition allows one-component moisture-curing adhesives, sealants or coatings that have good storage stability, long open times and cure quickly to give a surprisingly non-tacky material having pronounced high-resilient properties.

15 Claims, No Drawings

MOISTURE-CURING POLYURETHANE COMPOSITION CONTAINING OXAZOLIDINE

TECHNICAL FIELD

The invention relates to moisture-curing polyurethane compositions and to the use thereof as elastic adhesive, sealant or coating.

STATE OF THE ART

Polyurethane compositions which crosslink through reaction of isocyanate groups with moisture or water and cure to give elastomers are especially used as adhesives, sealants and coatings in the construction and manufacturing industry, for example for component bonding in assembly, for parquet bonding, for filling of joins or for roof sealing. Owing to their good adhesion and elasticity, they can gently damp forces acting on the substrates, triggered for instance by vibrations or variations in temperature. Especially in the case of application in a thick layer and/or over a large area, for instance in the case of connection joints or the bonding of large components with large dimensional tolerances or thermoplastic components, it is important that the elastomer is highly extensible and not too stiff, i.e. has a low modulus of elasticity, since the forces transmitted to the edges of the join or substrates otherwise become too high, resulting in component warpage, adhesive failure or substrate fracture, especially in the case of substrates having low resistance to tension, such as concrete or mortar. In the case of outdoor applications, this problem is aggravated by the diurnal and annual fluctuations in temperature, since the substrate gaps or joins to be bridged expand under cold conditions, and the elastomer simultaneously stiffens as it cools.

Suitable elastomers for such applications are those having soft-elastic properties, which have very high elastic extensibility coupled with low modulus of elasticity. Such elastomers are obtained especially with compositions comprising long-chain polymers and a low overall content of isocyanate groups. However, such compositions are often of low storage stability, especially when they contain a large amount of fillers and plasticizers that can introduce moisture, and they show marked surface tack, which lasts for a long time after application and leads to stains and reduced weathering resistance. Even the latent curing agents that are often used for reduction of blister formation in the course of curing bring only limited relief here, since these typically result in a certain stiffness, which is disadvantageous for soft-elastic properties. Many of these curing agents additionally also reduce storage stability in that they trigger premature crosslinking reactions of the isocyanate groups.

The prior art discloses monooxazolidines derived from aliphatic aldehydes or ketones, and the use thereof as moisture scavengers or desiccants for polyurethane compositions. Commercially available examples include 3-butyl-2-(3-heptyl)-1,3-oxazolidine based on N-butylaminoethanol and 2-ethylhexanal, for example as Incozol 2 (from Incorez), or 3-ethyl-2-methyl-2-(3-methylbutyl)-1,3-oxazolidine based on N-ethylaminoethanol and methyl isoamyl ketone, for example as Zoldine® MS-Plus (from Angus Chemical). Such desiccants are used in a small amount to scavenge water introduced into the composition via fillers and plasticizers. However, their storage stability is inadequate in many polyurethane compositions, especially those containing very reactive isocyanate groups derived from aromatic and/or sterically unhindered diisocyanates.

Also known are bisoxazolidines, which are used as latent curing agents in one-component polyurethanes. However, these are only of limited storage stability, and they cure to give comparatively stiff elastomers of not very high extensibility.

U.S. Pat. No. 6,255,433 discloses low-modulus one-component sealants comprising a polymer containing isocyanate groups derived from a mixture of polyol, monool and hydroxy-functional oxazolidine. However, such polymers containing isocyanate groups and having pendent oxazolidine groups are of high viscosity and are not very storage-stable. The sealants formulated therewith contain considerable amounts of xylene, which improves their storage stability but is undesirable for reasons of odor and VOC emissions. Furthermore, a monool is included in the preparation of the polymer. Although this lowers the modulus of elasticity, it leads to very tacky surfaces.

SUMMARY OF THE INVENTION

It is therefore an object of the present invention to provide a moisture-curing polyurethane composition which has excellent storage stability and cures rapidly and largely without blisters to give an elastomer having low surface tack, very high extensibility and very low modulus of elasticity.

It has been found that, surprisingly, this object is achieved by a polyurethane composition as described in claim 1. It comprises a polymer containing isocyanate groups and an oxazolidine of the formula (I) that is a monooxazolidine. The oxazolidine of the formula (I) enables very good storage stability, even in the case of very reactive diisocyanates, and, when a sufficient amount is used, largely blister-free curing, surprisingly resulting in a markedly soft-elastic material having a virtually tack-free surface. The N-substituted amino alcohol released from the oxazolidine of the formula (I) is difunctional with respect to isocyanate groups and forms a hard segment that segregates to a minor degree, and for that reason a comparatively plastic and tacky material would be expected in the case of use of higher amounts of oxazolidine. What is also surprising is good storage stability together with very reactive isocyanate groups, given that oxazolidines, for lack of storage stability, are otherwise used predominantly in slow-reacting compositions based on isophorone diisocyanate in particular. What is particularly surprising is good storage stability in compositions based on diphenylmethane 4,4'-diisocyanate, where the oxazolidines known from the prior art are of zero or only very limited storage stability.

The polyurethane composition of the invention enables elastic adhesives, sealants or coatings having markedly soft-elastic properties, which have good storage stability, cure rapidly and are free of tack even after a short time, i.e. lose their surface tack. As a result, they are protected even after a short time from staining, for example by construction dust, pollen or insects, and from weathering influences, and hence are esthetically pleasing and long-lived. On account of their low modulus of elasticity coupled with high extensibility, they are capable of damping even high forces and hence of transmitting them gently to the substrates, as a result of which there is no component warpage, substrate fracture or adhesive failure. Such products are usable advantageously for applications in a thick layer or over a large area, especially for joins or bonds where high tolerances have to be bridged.

Further aspects of the invention are the subject of further independent claims. Particularly preferred embodiments of the invention are the subject of the dependent claims.

WAYS OF EXECUTING THE INVENTION

The invention provides a polyurethane composition comprising at least one polymer containing isocyanate groups, obtained from the reaction of at least one polyol and at least one diisocyanate, and at least one oxazolidine of the formula (I)

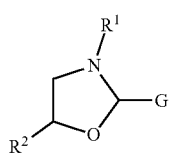

where
R$^1$ is an alkyl or cycloalkyl or arylalkyl radical having 1 to 8 carbon atoms,
R$^2$ is H or methyl, and
G is an aromatic radical selected from the group consisting of furanyl, thiophenyl, pyridinyl, indenyl, indanyl, benzodioxolyl, benzodioxanyl, naphthyl, tetrahydronaphthyl, anthracenyl and a radical of the formula

where
R$^3$ is fluoro, chloro, bromo, nitro, cyano, phenyl, phenoxy, (C$_1$ to C$_5$)-alkyl or (C$_1$ to C$_5$)-alkoxy, and
n is 0, 1, 2 or 3.
If n is 2 or 3, the R$^3$ radicals may be identical or different radicals.

An "aromatic" radical refers to one bonded to the particular molecule via an aromatic carbon atom.

"NCO content" refers to the content of isocyanate groups in % by weight.

An "aromatic" isocyanate group refers to one bonded directly to an aromatic carbon atom. Isocyanates having aromatic isocyanate groups are correspondingly referred to as "aromatic isocyanates".

An "aliphatic" isocyanate group refers to one bonded directly to an aliphatic or cycloaliphatic carbon atom. Isocyanates having exclusively aliphatic isocyanate groups are correspondingly referred to as "aliphatic isocyanates".

Substance names beginning with "poly", such as polyol or polyisocyanate, refer to substances that formally contain two or more of the functional groups that occur in their name per molecule.

"Molecular weight" refers to the molar mass (in g/mol) of a molecule or a molecule residue. "Average molecular weight" refers to the number-average molecular weight ($M_n$) of a polydisperse mixture of oligomeric or polymeric molecules or molecule residues. It is determined by means of gel permeation chromatography (GPC) against polystyrene as standard.

A substance or composition is referred to as "storage-stable" or "storable" when it can be stored at room temperature in a suitable container over a prolonged period, typically over at least 3 months to up to 6 months or more, without any change in its application or use properties to a degree of relevance for the use thereof as a result of the storage.

A dashed line in the formulae in this document in each case represents the bond between a substituent and the associated molecular radical.

"Room temperature" refers to a temperature of 23° C.

The polymer containing isocyanate groups preferably has an NCO content in the range from 0.5% to 5% by weight, preferably 0.75% to 3.2% by weight, especially 1% to 2.5% by weight. Such a polymer is a particularly long-chain polymer and enables high extensibility of the elastomer obtained therewith. However, on account of the low NCO content, it also achieves particularly high standards in relation to storage stability.

The polymer containing isocyanate groups preferably has an average molecular weight $M_n$ in the range from 2,000 to 20,000 g/mol, especially 4,000 to 15,000 g/mol.

The polymer containing isocyanate groups preferably has a low monomeric diisocyanate content, more preferably less than 2% by weight, especially less than 1% by weight.

The polymer containing isocyanate groups is especially obtained from the reaction of at least one polyol with a superstoichiometric amount of at least one diisocyanate. The reaction is preferably conducted with exclusion of moisture at a temperature in the range from 20 to 160° C., especially 40 to 140° C., optionally in the presence of suitable catalysts.

The NCO/OH ratio is preferably in the range from 1.3/1 to 10/1. The monomeric diisocyanate remaining in the reaction mixture after the reaction of the OH groups can be removed, especially by means of distillation.

If excess monomeric diisocyanate is removed by means of distillation, the NCO/OH ratio in the reaction is preferably in the range from 3/1 to 7/1, and the resultant polymer containing isocyanate groups, after the distillation, preferably contains not more than 0.5% by weight, more preferably not more than 0.3% by weight, of monomeric diisocyanate. Monomeric diisocyanate is especially removed by means of short-path distillation under reduced pressure.

If no excess monomeric diisocyanate is removed from the polymer, the NCO/OH ratio in the reaction is preferably in the range from 1.3/1 to 2.5/1.

The polymer is optionally prepared with additional use of plasticizers or solvents, in which case the plasticizers or solvents used do not contain any groups reactive toward isocyanates.

The diisocyanate is preferably a commercially available aliphatic, cycloaliphatic or aromatic diisocyanate, such as, in particular, hexamethylene 1,6-diisocyanate (HDI), 1-isocyanato-3,3,5-trimethyl-5-isocyanatomethylcyclohexane (isophorone diisocyanate or IPDI), perhydro(diphenylmethane 4,4'-diisocyanate) (H$_{12}$MDI), cyclohexane 1,3- or 1,4-diisocyanate, 1,3- or 1,4-bis(isocyanatomethyl)cyclohexane, m- or p-xylylene diisocyanate (XDI), tolylene 2,4-diisocyanate or mixtures thereof with tolylene 2,6-diisocyanate (TDI), diphenylmethane 4,4'-diisocyanate, optionally with fractions of diphenylmethane 2,4'- and/or 2,2'-diisocyanate (MDI), p-phenylene diisocyanate (PPDI) or naphthalene 1,5-diisocyanate (NDI).

The diisocyanate is preferably selected from the group consisting of HDI, H$_{12}$MDI, TDI and MDI. These diisocyanates are easily obtainable and particularly reactive.

But they also achieve particularly high standards in relation to storage stability.

Among these, preference is given to HDI, H$_{12}$MDI or MDI. These diisocyanates enable a particularly tack-free surface.

A particularly preferred diisocyanate is MDI, especially 4,4'-MDI containing at least 97% of the diphenylmethane 4,4'-diisocyanate isomer and not more than 3% of the other isomers. This affords polyurethane compositions having particularly rapid curing. But this also achieves very particularly high standards in the attainment of good storage stabilities and low moduli of elasticity.

Suitable polyols are commercial polyols or mixtures thereof, especially
   polyether polyols, especially polyoxyalkylenediols and/or polyoxyalkylenetriols, especially polymerization products of ethylene oxide or 1,2-propylene oxide or 1,2- or 2,3-butylene oxide or oxetane or tetrahydrofuran or mixtures thereof, where these may be polymerized with the aid of a starter molecule having two or three active hydrogen atoms, especially a starter molecule such as water, ammonia or a compound having multiple OH or NH groups, for example ethane-1,2-diol, propane-1,2- or -1,3-diol, neopentyl glycol, diethylene glycol, triethylene glycol, the isomeric dipropylene glycols or tripropylene glycols, the isomeric butanediols, pentanediols, hexanediols, heptanediols, octanediols, nonanediols, decanediols, undecanediols, cyclohexane-1,3- or -1,4-dimethanol, bisphenol A, hydrogenated bisphenol A, 1,1,1-trimethylolethane, 1,1,1-trimethylolpropane, glycerol or aniline, or mixtures of the aforementioned compounds. Likewise suitable are polyether polyols with polymer particles dispersed therein, especially those with styrene/acrylonitrile (SAN) particles or polyurea or polyhydrazodicarbonamide (PHD) particles.

Preferred polyether polyols are polyoxypropylene diols or polyoxypropylene triols, or what are called ethylene oxide-terminated (EO-capped or EO-tipped) polyoxypropylene diols or triols. The latter are mixed polyoxyethylene/polyoxypropylene polyols which are especially obtained in that polyoxypropylene diols or triols, on conclusion of the polypropoxylation reaction, are further alkoxylated with ethylene oxide and hence have primary hydroxyl groups.

Preferred polyether polyols have a level of unsaturation of less than 0.02 meq/g, especially less than 0.01 meq/g.

Polyester polyols, also called oligoesterols, prepared by known processes, especially the polycondensation of hydroxycarboxylic acids or lactones or the polycondensation of aliphatic and/or aromatic polycarboxylic acids with di- or polyhydric alcohols.

Polycarbonate polyols.
   Polyether polyester polyols.
   Polyacrylate or polymethacrylate polyols.
   Polyhydroxy-functional fats or oils, for example natural fats and oils, especially castor oil, or polyols obtained by chemical modification of natural fats and oils— called oleochemical polyols.
   Polyhydrocarbon polyols, also called oligohydrocarbonols, such as, in particular, polyhydroxy-functional polyolefins, polyisobutylenes, polyisoprenes; polyhydroxy-functional ethylene/propylene, ethylene/butylene or ethylene/propylene/diene copolymers, as produced, for example, by Kraton Polymers; polyhydroxy-functional polymers of dienes, especially of 1,3-butadiene, which can especially also be prepared from anionic polymerization;
   polyhydroxy-functional copolymers of dienes, such as 1,3-butadiene, or diene mixtures and vinyl monomers, such as styrene, acrylonitrile, vinyl chloride, vinyl acetate, vinyl alcohol, isobutylene or isoprene, especially polyhydroxy-functional acrylonitrile/butadiene copolymers, as can be prepared, in particular, from epoxides or amino alcohols and carboxyl-terminated acrylonitrile/butadiene copolymers (commercially available, for example, under the Hypro® CTBN or CTBNX or ETBN name from Emerald Performance Materials); or hydrogenated polyhydroxy-functional polymers or copolymers of dienes.

Also especially suitable are mixtures of polyols.

Preference is given to polyether polyols, especially polyoxyalkylenedi- or -triols.

Particular preference is given to polyoxypropylenedi- or -triols optionally having terminal oxyethylene groups.

Preference is given to polyols having an average molecular weight M$_n$ in the range from 1,000 to 20,000 g/mol, preferably from 2,000 to 15,000 g/mol. Preference is given to polyols having an average OH functionality in the range from 1.6 to 3.

The preferred polyols enable particularly soft and stable elastomers.

In the preparation of a polymer containing isocyanate groups, it is also possible to include proportions of di- or polyfunctional alcohols, especially ethane-1,2-diol, propane-1,2-diol, propane-1,3-diol, 2-methylpropane-1,3-diol, butane-1,4-diol, pentane-1,3-diol, pentane-1,5-diol, 3-methylpentane-1,5-diol, neopentyl glycol, hexane-1,6-diol, diethylene glycol, triethylene glycol, dipropylene glycol, tripropylene glycol, cyclohexane-1,3- or -1,4-dimethanol, ethoxylated bisphenol A, propoxylated bisphenol A, cyclohexanediol, or alkoxylated derivatives of the alcohols mentioned or mixtures of the alcohols mentioned.

In a preferred embodiment, the polyol contains at least one triol. This affords a polymer containing isocyanate groups and having a particularly high NCO functionality, which enables a particular tack-free surface with the oxazolidine of the formula (I). The polyol used is preferably a mixture of one or more diols and one or more triols.

This embodiment of the invention is advantageous especially when the composition does not include any further reactive constituents having a functionality of more than 2, for example diisocyanate oligomers or trialdimines.

The polyurethane composition of the invention comprises at least one oxazolidine of the formula (I).

Preferably, R$^1$ is methyl, ethyl, n-propyl, n-butyl, n-hexyl, cyclohexyl, 2-ethylhexyl, or benzyl. These oxazolidines are particularly easily obtainable.

More preferably, R$^1$ is methyl, ethyl, n-butyl or benzyl.

Most preferably, R$^1$ is butyl. This affords polyurethane compositions having a particularly attractive combination of good storage stability, rapid curing and soft-elastic properties.

Preferably, R$^2$ is H.

Preferably, G is furan-2-yl, 1,3-benzodioxol-5-yl, 1-naphthyl or a radical of the formula

Preferably, R$^3$ is (C$_1$ to C$_4$)-alkyl or (C$_1$ to C$_4$)-alkoxy, especially methyl or methoxy.

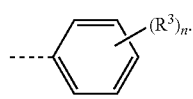

More preferably, G is a radical of the formula Such an oxazolidine has the formula (Ia)

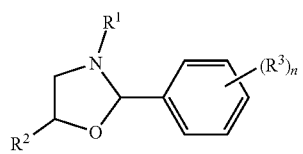

where $R^1$, $R^2$, $R^3$ and n have the definitions already given.

Preferably, n is 0 or 1 or 2, especially 0 or 1.

Most preferably, G is phenyl, 2-methylphenyl, 3-methylphenyl, 4-methylphenyl, 4-isopropylphenyl or 4-methoxyphenyl, especially phenyl.

More preferably, the oxazolidine of the formula (I) is selected from the group consisting of

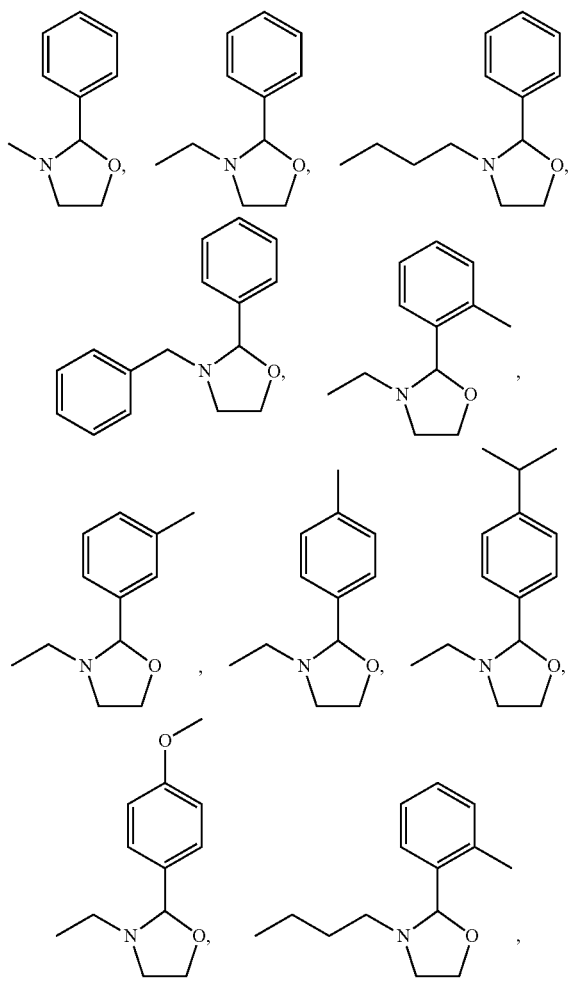

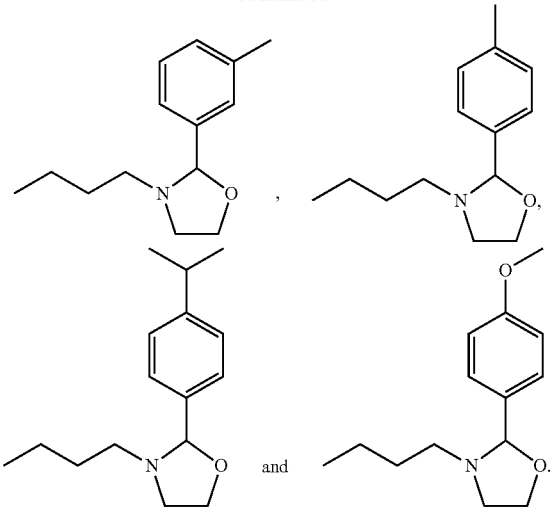

The preferred oxazolidines of the formula (I) are easily obtainable, are liquid and of low viscosity at room temperature, have good storage stability together with reactive isocyanate groups, and enable rapid curing.

The oxazolidine of the formula (I) is preferably obtained from the reaction of at least one amino alcohol of the formula (II) with at least one aldehyde of the formula (III) in a condensation reaction with removal of water;

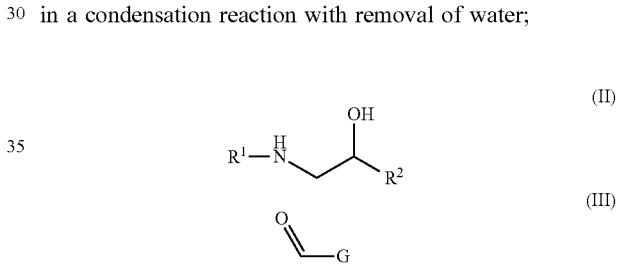

where $R^1$, $R^2$, and G have the definitions already given.

The aldehyde is used here at least stoichiometrically in relation to the NH groups.

Preference is given to running the reaction in such a way that the amino alcohol of the formula (II) is combined with the aldehyde of the formula (III) to give a reaction mixture, and the water of condensation and any solvent and/or excess aldehyde present are removed from the reaction mixture by a suitable method during or after the combination, optionally while heating and/or applying reduced pressure.

A suitable amino alcohol of the formula (II) is especially N-methylethanolamine, N-ethylethanolamine, N-n-propylethanolamine, N-isopropylethanolamine, N-n-butylethanolamine, N-isobutylethanolamine, N-2-butylethanolamine, N-tert-butylethanolamine, N-n-hexylethanolamine, N-isohexylethanolamine, N-(2-ethylhexyl)ethanolamine, N-cyclohexylethanolamine or N-benzylethanolamine, especially N-methylethanolamine, N-ethylethanolamine, N-n-butylethanolamine or N-benzylethanolamine. Particular preference is given to N-n-butylethanolamine.

A suitable aldehyde of the formula (III) is especially furan-2-carbaldehyde (furfural), furan-3-carbaldehyde, thiophene-2-carbaldehyde, thiophene-3-carbaldehyde, pyridine-2-carbaldehyde, pyridine-3-carbaldehyde (nicotinaldehyde), pyridine-4-carbaldehyde (isonicotinaldehyde), 1H-indene-4-carbaldehyde, 1H-indene-5-carbaldehyde, 1H-indene-6- carbaldehyde, 1H-indene-7-carbaldehyde, 4-indanecarbaldehyde, 5-indanecarbaldehyde, 1,3-benzodioxole-4-carbaldehyde, 1,3-benzodioxole-5-carbaldehyde, 1,4-benzodioxane-5-carbaldehyde, 1,4-benzodioxane-6-carbaldehyde, 1-naphthaldehyde, 2-naphthaldehyde, 5,6,7,8-tetrahydro-1-naphthaldehyde, 5,6,7,8-tetrahydro-2-naphthaldehyde, 9-anthracenecarbaldehyde, benzaldehyde, 2-fluorobenzaldehyde, 3-fluorobenzaldehyde, 4-fluorobenzaldehyde, 2-chlorobenzaldehyde, 3-chlorobenzaldehyde, 4-chlorobenzaldehyde, 2,4-dichlorobenzaldehyde, 3,4-dichlorobenzaldehyde, 3,5-dichlorobenzaldehyde, 2-bromobenzaldehyde, 3-bromobenzaldehyde, 4-bromobenzaldehyde, 2-nitrobenzaldehyde, 3-nitrobenzaldehyde, 4-nitrobenzaldehyde, 2,4-dinitrobenzaldehyde, 3,5-dinitrobenzaldehyde, 2-cyanobenzaldehyde, 4-cyanobenzaldehyde, 4-phenylbenzaldehyde (biphenyl-4-carbaldehyde), 3-phenoxybenzaldehyde, 4-phenoxybenzaldehyde, 2-methylbenzaldehyde (o-tolualdehyde), 3-methylbenzaldehyde (m-tolualdehyde), 4-methylbenzaldehyde (p-tolualdehyde), 2,4-dimethylbenzaldehyde, 2,5-dimethylbenzaldehyde, 2,4,6-trimethylbenzaldehyde (mesitylaldehyde), 4-ethylbenzaldehyde, 4-isopropylbenzaldehyde (cuminaldehyde), 4-tert-butylbenzaldehyde, 2-methoxybenzaldehyde (o-anisaldehyde), 3-methoxybenzaldehyde (m-anisaldehyde), 4-methoxybenzaldehyde (anisaldehyde), 2,3-dimethoxybenzaldehyde, 2,4-dimethoxybenzaldehyde, 2,5-dimethoxybenzaldehyde, 3,4-dimethoxybenzaldehyde (veratrumaldehyde), 3,5-dimethoxybenzaldehyde, 2,4,6-trimethylbenzaldehyde, 2,4,5-trimethoxybenzaldehyde (asaronaldehyde), 2,4,6-trimethoxybenzaldehyde, 3,4,5-trimethoxybenzaldehyde, 2-ethoxybenzaldehyde, 4-ethoxybenzaldehyde or 4-butoxybenzaldehyde.

Preference is given to furan-2-carbaldehyde, 1,3-benzodioxole-5-carbaldehyde, 1-naphthaldehyde, benzaldehyde, 2-methylbenzaldehyde, 3-methylbenzaldehyde, 4-methylbenzaldehyde, 4-isopropylbenzaldehyde or 4-methoxybenzaldehyde. Particular preference is given to benzaldehyde.

On hydrolysis, the oxazolidine of the formula (I) releases the parent amino alcohol of the formula (II) and the aldehyde of the formula (III). The amino alcohol reacts here with isocyanate groups present, reaction of the amino group being much faster than that of the hydroxyl group and water present.

In the polyurethane composition of the invention, the numerical ratio between oxazolidine groups and isocyanate groups is preferably in the range from 0.1 to 0.5.

The numerical ratio between oxazolidine groups and isocyanate groups is more preferably in the range from 0.2 to 0.45. In this range, the oxazolidine of the formula (I) acts not just as a desiccant but also as a latent curing agent. This enables largely blister-free curing and markedly soft-elastic properties.

In a preferred embodiment of the invention, the polyurethane composition of the invention, in addition to the oxazolidine of the formula (I), comprises at least one aldimine of the formula

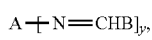

where y is 2 or 3, A is an organic radical having 2 to 25 carbon atoms, and B is an organic radical having 3 to 30 carbon atoms, especially 4 to 23 carbon atoms.

The aldimine of the formula

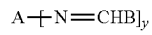

is preferably an aldimine of the formula (IV) or (V)

 (IV)

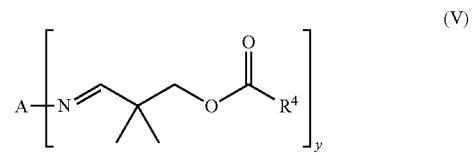 (V)

where
$R^4$ is H or an alkyl radical having 1 to 17 carbon atoms, especially a linear alkyl radical having 1 to 11 carbon atoms, and G, A and y have the definitions already given.

A is preferably an alkylene radical optionally having cyclic components or a di- or trivalent polyoxyalkylene radical having 5 to 15 carbon atoms, especially 1,6-hexylene, (1,5,5-trimethylcyclohexan-1-yl)methane-1,3 or α,ω-polyoxypropylene having an average molecular weight in the range from 170 to 300 g/mol or trimethylolpropane-started tris(ω-polyoxypropylene) having an average molecular weight in the range from 330 to 500 g/mol.

Preferably, G is phenyl, 2-methylphenyl, 3-methylphenyl, 4-methylphenyl, 4-isopropylphenyl or 4-methoxyphenyl, especially phenyl.

Preferably, $R^4$ is methyl or lauryl.

An aldimine of the formula

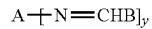

is especially obtained by reaction of an amine of the formula A-$(NH_2)_y$ with an aldehyde of the formula O=CHB, with removal of water of condensation.

Preferred amines A-$(NH_2)_y$ are aliphatic or cycloaliphatic primary di- or triamines, especially hexamethylene-1,6-diamine, isophoronediamine, α,ω-polyoxypropylenediamines having an average molecular weight in the range from 200 to 350 g/mol, especially Jeffamine® D-230 (from Huntsman Corp.), or trimethylolpropane-started tris(ω-polyoxypropyleneamine), especially Jeffamine® T-403 (from Huntsman Corp.).

A preferred aldehyde of the formula O=CHB is benzaldehyde, 2-methylbenzaldehyde, 3-methylbenzaldehyde, 4-methylbenzaldehyde, 4-isopropylbenzaldehyde, 4-methoxybenzaldehyde or aldol esters of carboxylic acids, especially 2,2-dimethyl-3-acetoxypropanal or 2,2-dimethyl-3-lauroxyloxypropanal.

If the polyurethane composition of the invention comprises at least one aldimine of the formula

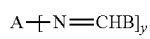

the numerical ratio between oxazolidine groups and isocyanate groups is preferably in the range from 0.1 to 0.3, and the numerical ratio between the sum total of oxazolidine groups plus aldimine groups and the isocyanate groups is preferably in the range from 0.3 to 0.8.

A combination of oxazolidine of the formula (I) and aldimine enables very storage-stable soft-elastic compositions having very rapid curing.

The polyurethane composition preferably comprises at least one further constituent, especially selected from the group consisting of fillers, plasticizers, diisocyanate oligomers, catalysts and stabilizers.

Suitable fillers are especially ground or precipitated calcium carbonates, optionally coated with fatty acids, especially stearates, barytes, quartz flours, quartz sands, dolomites, wollastonites, calcined kaolins, sheet silicates, such as mica or talc, zeolites, aluminum hydroxides, magnesium hydroxides, silicas, including finely divided silicas from pyrolysis processes, cements, gypsums, fly ashes, industrially produced carbon blacks, graphite, metal powders, for example of aluminum, copper, iron, silver or steel, PVC powders or hollow beads.

Preference is given to calcium carbonates that have optionally been coated with fatty acids, especially stearates, calcined kaolins, finely divided silicas or industrially produced carbon blacks.

Suitable plasticizers are especially carboxylic esters, such as phthalates, especially diisononyl phthalate (DINP), diisodecyl phthalate (DIDP) or di(2-propylheptyl)phthalate (DPHP), hydrogenated phthalates or cyclohexane-1,2-dicarboxylates, especially hydrogenated diisononyl phthalate or diisononyl cyclohexane-1,2-dicarboxylate (DINCH), terephthalates, especially bis(2-ethylhexyl) terephthalate (DOTP) or diisononyl terephthalate (DINT), hydrogenated terephthalates or cyclohexane-1,4-dicarboxylates, especially hydrogenated bis(2-ethylhexyl) terephthalate or bis(2-ethylhexyl) cyclohexane-1,4-dicarboxylate, or hydrogenated diisononyl terephthalate or diisononyl cyclohexane-1,4-dicarboxylate, isophthalates, trimellitates, adipates, especially dioctyl adipate, azelates, sebacates, benzoates, glycol ethers, glycol esters, plasticizers having polyether structure, especially polypropylene oxide monools, diols or triols having blocked hydroxyl groups, especially in the form of acetate groups, organic phosphoric or sulfonic esters, polybutenes, polyisobutenes or plasticizers derived from natural fats or oils, especially epoxidized soybean or linseed oil.

Preferred plasticizers are phthalates or plasticizers having polyether structure.

Suitable diisocyanate oligomers are especially HDI biurets such as Desmodur® N 100 or N 3200 (from Covestro AG), Tolonate® HDB or HDB-LV (from Vencorex) or Duranate® 24A-100 (from Asahi Kasei); HDI isocyanurates such as Desmodur® N 3300, N 3600 or N 3790 BA (all from Covestro), Tolonate® HDT, HDT-LV or HDT-LV2 (from Vencorex), Duranate® TPA-100 or THA-100 (from Asahi Kasei) or Coronate® HX (from Tosoh Corp.); HDI uretdiones such as Desmodur® N 3400 (from Covestro); HDI iminooxadiazinediones such as Desmodur® XP 2410 (from Covestro); HDI allophanates such as Desmodur® VP LS 2102 (from Covestro); IPDI isocyanurates, for example in solution as Desmodur® Z 4470 (from Covestro) or in solid form as Vestanat® T1890/100 (from Evonik Industries); TDI oligomers such as Desmodur® IL (from Covestro); or mixed isocyanurates based on TDI/HDI, such as Desmodur® HL (from Covestro).

Suitable catalysts for the acceleration of the reaction of isocyanate groups are especially organotin(IV) compounds such as, in particular, dibutyltin diacetate, dibutyltin dilaurate, dibutyltin dichloride, dibutyltin diacetylacetonate, dimethyltin dilaurate, dioctyltin diacetate, dioctyltin dilaurate or dioctyltin diacetylacetonate, complexes of bismuth(III) or zirconium(IV), especially with ligands selected from alkoxides, carboxylates, 1,3-diketonates, oxinate, 1,3-ketoesterates and 1,3-ketoamidates, or compounds containing tertiary amino groups, such as especially 2,2'-dimorpholinodiethyl ether (DMDEE).

Suitable catalysts for the acceleration of the hydrolysis of the oxazolidine or any further latent curing agents present are especially organic acids, especially carboxylic acids such as 2-ethylhexanoic acid, lauric acid, stearic acid, isostearic acid, oleic acid, neodecanoic acid, benzoic acid, salicylic acid or 2-nitrobenzoic acid, organic carboxylic anhydrides such as phthalic anhydride, hexahydrophthalic anhydride or methylhexahydrophthalic anhydride, silyl esters of carboxylic acids, organic sulfonic acids such as methanesulfonic acid, p-toluenesulfonic acid or 4-dodecylbenzenesulfonic acid, sulfonic esters, other organic or inorganic acids, or mixtures of the aforementioned acids and esters. Particular preference is given to carboxylic acids, especially aromatic carboxylic acids, such as benzoic acid, 2-nitrobenzoic acid or especially salicylic acid.

Also especially suitable are combinations of different catalysts.

Suitable stabilizers are especially stabilizers against oxidation, heat, light or UV radiation, especially titanium dioxides, iron oxides, zinc oxides, benzophenones, benzotriazoles, compounds having 2,6-di-tert-butylphenol groups, as known, for example, under the Irganox® trade name (from BASF), compounds having 2,2,6,6-tetramethylpiperidine groups, called HALS (hindered amine light stabilizers), as known, for example, under the Tinuvin® trade name (from BASF), or phosphorus-containing compounds as known, for example, under the Irgafos® trade name (from BASF).

The polyurethane composition may contain further additions, especially inorganic or organic pigments, especially titanium dioxide, chromium oxides or iron oxides;

fibers, especially glass fibers, carbon fibers, metal fibers, ceramic fibers, polymer fibers, such as polyamide fibers or polyethylene fibers, or natural fibers, such as wool, cellulose, hemp or sisal;

nanofillers such as graphene or carbon nanotubes;

dyes;

further latent curing agents, especially further oxazolidines, aldimines, ketimines or enamines;

further isocyanates, especially a room temperature liquid form of MDI, especially a 4,4'-MDI liquefied by carbodiimidization or uretonimine formation or adduct formation with polyols, or a mixture of MDI monomers with MDI homologs (polymeric MDI or PMDI);

further desiccants, especially molecular sieve powder, calcium oxide, highly reactive isocyanates, such as p-tosyl isocyanate, or orthoformic esters;

adhesion promoters, especially organoalkoxysilanes, especially epoxysilanes, such as especially 3-glycidoxypropyltrimethoxysilane or 3-glycidoxypropyltriethoxysilane, (meth)acrylosilanes, anhydridosilanes, carbamatosilanes, alkylsilanes or iminosilanes, or oligomeric forms of these silanes, or titanates;

further catalysts which accelerate the reaction of the isocyanate groups;

rheology modifiers, especially thickeners, especially sheet silicates, such as bentonites, derivatives of castor oil, hydrogenated castor oil, polyamides, polyamide waxes, polyurethanes, urea compounds, fumed silicas, cellulose ethers or hydrophobically modified polyoxyethylenes;

solvents, especially acetone, methyl acetate, tert-butyl acetate, 1-methoxy-2-propyl acetate, ethyl 3-ethoxypropionate, diisopropyl ether, diethylene glycol diethyl ether, ethylene glycol diethyl ether, ethylene glycol monobutyl ether, ethylene glycol mono-2-ethylhexyl ether, acetals such as propylal, butylal, 2-ethylhexylal, dioxolane, glycerol formal or 2,5,7,10-tetraoxaundecane (TOU), toluene, xylene, heptane, octane, naphtha, white spirit, petroleum ether or gasoline, especially Solvesso™ grades (from ExxonMobil Chemical Co.), and propylene carbonate, dimethyl carbonate, butyrolactone, N-methylpyrrolidone, N-ethylpyrrolidone, p-chlorobenzotrifluoride or benzotrifluoride;

natural resins, fats or oils, such as rosin, shellac, linseed oil, castor oil or soybean oil;

nonreactive polymers, especially homo- or copolymers of unsaturated monomers, especially from the group comprising ethylene, propylene, butylene, isobutylene, isoprene, vinyl acetate or alkyl (meth)acrylates, especially polyethylenes (PE), polypropylenes (PP), polyisobutylenes, ethylene/vinyl acetate copolymers (EVA) or atactic poly-α-olefins (APAO);

flame-retardant substances, especially the aluminum hydroxide or magnesium hydroxide fillers already mentioned, and also especially organic phosphoric esters, such as especially triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl) phosphate, tris(chloropropyl) phosphate, isopropylated triphenyl phosphate, mono-, bis- or tris(isopropylphenyl) phosphates of different degrees of isopropylation, resorcinol bis(diphenylphosphate), bisphenol A bis(diphenylphosphate) or ammonium polyphosphates;

additives, especially wetting agents, leveling agents, defoamers, deaerating agents, further stabilizers or biocides;

or further substances customarily used in moisture-curing polyurethane compositions.

It may be advisable to chemically or physically dry certain substances before mixing them into the composition.

Preferably, the polyurethane composition of the invention contains little solvent. It especially contains less than 10% by weight, preferably less than 5% by weight, more preferably less than 2.5% by weight, of solvent.

The polyurethane composition of the invention preferably contains

10% to 50% by weight of polymer containing isocyanate groups and having an NCO content in the range from 0.5% to 5% by weight, obtained from the reaction of at least one polyol and at least one diisocyanate selected from the group consisting of HDI, $H_{12}$MDI, TDI and MDI, 0.1% to 5% by weight of oxazolidine of the formula (I), 20% to 60% by weight of fillers, 10% to 40% by weight of plasticizers, and optionally further constituents, especially aldimines, diisocyanate oligomers, catalysts or stabilizers.

The polyurethane composition is especially produced with exclusion of moisture and stored at ambient temperature in moisture-tight containers. A suitable moisture-tight container especially consists of an optionally coated metal and/or plastic, and is especially a drum, a transport box, a hobbock, a bucket, a canister, a can, a bag, a tubular bag, a cartridge or a tube.

The polyurethane composition may be in the form of a one-component composition or in the form of a multicomponent, in particular two-component, composition.

A composition referred to as a "one-component" composition is one in which all constituents of the composition are in the same container, which is storage-stable per se and which is curable with moisture.

A composition referred to as a "two-component" composition is one in which the constituents of the composition are in two different components which are stored in separate containers and are not mixed with one another until shortly before or during the application of the composition.

The polyurethane composition is preferably a one-component moisture-curing composition. Given suitable packaging and storage, it is storage-stable, typically over several months, up to one year or longer.

On curing, the isocyanate groups react under the influence of moisture with the amino and hydroxyl groups released from the oxazolidine of the formula (I) and with any other latent curing agents present. Some of the isocyanate groups, especially the excess isocyanate groups relative to the reactive groups released, react with one another under the influence of moisture. The totality of these reactions of isocyanate groups that lead to the curing of the composition is also referred to as crosslinking.

The moisture required for curing of the polyurethane composition preferably gets into the composition applied through diffusion from the air (atmospheric moisture).

In the process, a solid layer of cured composition (skin) is formed on the surfaces of the composition which come into contact with air. The curing continues in the direction of diffusion from the outside inward, the skin becoming increasingly thick and ultimately encompassing the entire composition applied. The moisture can also get into the composition additionally or entirely from one or more substrate(s) to which the composition has been applied and/or can come from an accelerator component which is mixed into the composition on application or is contacted therewith after application, for example by painting or spraying.

The polyurethane composition is preferably applied at ambient temperature, especially in the range from about −10 to 50° C., preferably in the range from −5 to 45° C., especially 0 to 40° C.

The composition is preferably likewise cured at ambient temperature.

The curing results in the cured composition.

The polyurethane composition has a comparatively long open time coupled with rapid curing.

The "open time" refers to the period of time over which the composition can be worked or reworked after the curing process has commenced.

The time until formation of a skin (skin time) is a measure of the open time.

The curing releases an aldehyde of the formula (III) and possibly further aldehydes. Depending on its size, this is more or less volatile and can evaporate out of or remain in the cured composition.

The polyurethane composition is preferably used as an adhesive or sealant or coating, where the adhesive or sealant or coating is especially soft-elastic.

As adhesive and/or sealant, the composition is especially suitable for adhesive and sealing applications, especially in the building and manufacturing industry or in motor vehicle construction, especially for parquet bonding, cavity sealing, or sealing of joins, seams or cavities, especially for joins in construction such as expansion joints or connection joints between components. A sealant having soft-elastic properties is particularly suitable especially for the sealing of expansion joints in built structures.

As coating, the composition is suitable for protection of floors or walls, especially as what is called a liquid-applied membrane for sealing of roofs, especially flat roofs or slightly inclined roof areas or gardens, or in building interiors for water sealing, for example beneath tiles or ceramic slabs in wet cells or kitchens, or as seam seal.

It can also be used for repair purposes as seal or coating, for example of leaking roof membranes or other elastic seals.

The polyurethane composition may be formulated in such a way that it has a pasty consistency with a high yield point, especially for use as an adhesive or sealant. Such a composition can be applied by spatula or under pressure by means of a suitable device, for example by means of a tube, a cartridge gun or a drum pump or an application robot, wherein the composition is optionally discharged in the form of a bead having an essentially round or triangular cross-sectional area. The layer thickness of the composition applied is especially in the range from 0.5 to 50 mm, preferably 1 to 30 mm.

The polyurethane composition can also be formulated such that it is fluid and "self-leveling" or only slightly thixotropic, especially for use as sealing compound or coating. Such a composition can be applied by pouring it out or by spatula. As a coating, it can then be distributed over an area to give the desired layer thickness, for example by means of a roll, doctor blade, notched trowel or rubber squeegee. In one operation, typically a layer thickness in the range from 0.5 to 5 mm, especially 1 to 3 mm, is applied.

Suitable substrates which can be bonded or sealed or coated with the composition are especially glass, glass ceramic, concrete, mortar, cement screed, fiber cement, especially fiber cement boards, brick, tile, gypsum, especially gypsum boards, or natural stone, such as granite or marble;

repair or leveling compounds based on PCC (polymer-modified cement mortar) or ECC (epoxy resin-modified cement mortar);

metals or alloys, such as aluminum, copper, iron, steel, nonferrous metals, including surface-finished metals or alloys, such as zinc-plated or chromium-plated metals;

asphalt or bitumen;

leather, textiles, paper, wood, wood materials bonded with resins, such as phenolic, melamine or epoxy resins, resin/textile composites or further materials called polymer composites;

plastics, such as rigid and flexible PVC, polycarbonate, polystyrene, polyester, polyamide, PMMA, ABS, SAN, epoxy resins, phenolic resins, PUR, POM, TPO, PE, PP, EPM or EPDM, in each case untreated or surface-treated, for example by means of plasma, corona or flames;

fiber-reinforced plastics, such as carbon fiber-reinforced plastics (CFP), glass fiber-reinforced plastics (GFP) and sheet molding compounds (SMC);

insulation foams, especially made of EPS, XPS, PUR, PIR, rock wool, glass wool or foamed glass;

coated or painted substrates, especially painted tiles, coated concrete, powder-coated metals or alloys or painted metal sheets;

paints or varnishes, especially automotive topcoats.

If required, the substrates can be pretreated prior to application, especially by physical and/or chemical cleaning methods or the application of an activator or a primer.

It is possible to bond and/or seal two identical or two different substrates.

The invention further provides a method of bonding and/or sealing, comprising the steps of
(i) applying the polyurethane composition described
to a first substrate and contacting the composition with at least one second substrate within the open time of the composition, or
to a first and to a second substrate and joining the two substrates within the open time of the composition, or
between at least two substrates,
(ii) curing the composition by contact with moisture.

The invention further provides a method of coating and/or sealing, comprising the steps of
(i) applying the polyurethane composition described to at least one substrate,
(ii) curing the composition by contact with moisture.

In the case of a two- or multicomponent composition, the components are mixed prior to step (i) in each case.

The invention further provides an article which is obtained from the method of bonding and/or sealing or the method of coating and/or sealing. This has been bonded, sealed or coated with the polyurethane composition described.

The article is especially a built structure above or below ground or part thereof, especially a bridge, a roof, a stairway, a floor or a facade, or an installable component thereof, or is an industrial good for a consumer good, especially a window, a domestic appliance or a mode of transport, or an installable component thereof.

The polyurethane composition of the invention has advantageous properties. It is storage-stable with exclusion of moisture. It has a sufficiently long open time to be reworkable over a certain period of time after application. Curing proceeds quickly, reliably and largely without blistering, and so the composition can be used without limitation even under climatically unfavorable conditions, such as high air humidity and/or high temperature or with use of aqueous accelerator components. The cured surface formed is surprisingly tack-free after a short time, which is difficult to achieve for a markedly soft-elastic material and is very valuable especially in the case of use on construction sites. Curing leads to a soft-elastic material that has very high elastic extensibility coupled with a low modulus of elasticity.

Examples

Working examples are adduced hereinafter, which are intended to elucidate the invention described. The invention is of course not limited to these described working examples.

"Standard climatic conditions" ("SCC") refer to a temperature of 23±1° C. and a relative air humidity of 50±5%.

Unless otherwise stated, the chemicals used were from Sigma-Aldrich Chemie GmbH.

Preparation of Oxazolidines:

The amine value (including blocked amino groups) was determined by means of titration (with 0.1N $HClO_4$ in acetic acid versus crystal violet).

Viscosity was measured with a thermostated Rheotec RC30 cone-plate viscometer (cone diameter 20 mm, cone angle 1°, cone tip-plate distance 0.05 mm, shear rate 150 $s^{-1}$ for viscosities<7 mPa·s, shear rate 100 $s^{-1}$ for viscosities of 7 to 100 mPa·s, shear rate 10 $s^{-1}$ for viscosities>0.1 Pas).

Infrared spectra (FT-IR) were measured as undiluted films on a Nicolet iS5 FT-IR instrument from Thermo Scientific equipped with a horizontal ATR measurement unit with a diamond crystal. The absorption bands are reported in wavenumbers (cm$^{-1}$).

Oxazolidine Ox-1:
3-Methyl-2-phenyl-1,3-oxazolidine

To an initial charge of 26.29 g of N-methylethanolamine in a round-bottom flask with a water separator (Dean-Stark apparatus) were added 37.88 g of benzaldehyde, 65 ml of cyclohexane and 1.25 g of salicylic acid, and the reaction mixture was boiled under reflux at 120° C. until all the water had separated out. Subsequently, the reaction mixture was cooled down and filtered, and the volatile constituents were removed under reduced pressure on a rotary evaporator at 80° C. What was obtained was a yellowish liquid having a viscosity of 5.6 mPa·s at 20° C., an amine value of 333 mg KOH/g and a calculated oxazolidine equivalent weight of 163.2 g/eq.

FT-IR: 3030, 2974, 2947, 2885, 2843, 2792, 2709, 1702, 1595, 1491, 1456, 1419, 1380, 1339, 1308, 1292, 1249, 1220, 1205, 1160, 1101, 1052, 1036, 1026, 975, 956, 922, 887, 860, 843, 754, 698.

Oxazolidine Ox-2:
3-Ethyl-2-phenyl-1,3-oxazolidine 31.20 g of N-ethylethanolamine was reacted as described for oxazolidine Ox-1 with 37.88 g of benzaldehyde. What was obtained was a yellowish liquid having a viscosity of 6.1 mPa·s at 20° C., an amine value of 308 mg KOH/g and a calculated oxazolidine equivalent weight of 177.3 g/eq.

Oxazolidine Ox-3: 3-Butyl-2-phenyl-1,3-oxazolidine
41.02 g of N-n-butylethanolamine was reacted as described for oxazolidine Ox-1 with 37.88 g of benzaldehyde. What was obtained was a yellowish liquid having a viscosity of 8.6 mPa·s at 20° C., an amine value of 267 mg KOH/g and a calculated oxazolidine equivalent weight of 205.3 g/eq.

FT-IR: 2955, 2931, 2872, 2801, 2714, 1704, 1593, 1492, 1456, 1377, 1342, 1307, 1292, 1248, 1215, 1203, 1178, 1152, 1086, 1063, 956, 924, 912, 844, 756, 736, 695.

Oxazolidine Ox-4:
3-Benzyl-2-phenyl-1,3-oxazolidine 52.92 g of N-benzylethanolamine was reacted as described for oxazolidine Ox-1 with 37.88 g of benzaldehyde. What was obtained was a yellowish liquid having a viscosity of 71 mPa·s at 20° C., an amine value of 230 mg KOH/g and a calculated oxazolidine equivalent weight of 239.3 g/eq.

FT-IR: 3061, 3028, 2942, 2884, 2801, 2713, 1952, 1882, 1811, 1703, 1604, 1586, 1494, 1454, 1385, 1371, 1340, 1307, 1292, 1252, 1215, 1203, 1161, 1127, 1101, 1056, 1025, 1001, 957, 922, 912, 889, 847, 757, 737, 696.

Oxazolidine Ox-5: 2,3-Diphenyl-1,3-oxazolidine 48.01 g of N-phenylethanolamine (aniline-ethanol) was reacted as described for oxazolidine Ox-1 with 37.88 g of benzaldehyde. What was obtained was a yellowish liquid having an amine value of 250 mg KOH/g and a calculated oxazolidine equivalent weight of 225.3 g/eq, which crystallized gradually at room temperature.

Oxazolidine Ox-6: Bisoxazolidine (1,6-bis((2-(2-phenyl-1,3-oxazolidin-3-yl)ethoxy)carbonylamino) hexane)

3-(2-Hydroxyethyl)-2-phenyl-1,3-oxazolidine was first prepared by reacting 63.09 g of diethanolamine as described for oxazolidine Ox-1 with 37.88 g of benzaldehyde. A dark yellow liquid having an amine value of 288.2 mg KOH/g was obtained. 37.80 g of the product obtained was initially charged in a round-bottom flask under a nitrogen atmosphere and heated up. At 80° C., 8.33 g of hexamethylene 1,6-diisocyanate was added dropwise and then the mixture was stirred at 80° C. until no isocyanate groups were detectable any longer by means of IR spectroscopy. What was obtained was a yellow material that was solid at room temperature and had an amine value of 181.4 mg KOH/g and a calculated oxazolidine equivalent weight of 279 g/eq, and which had a viscosity at 60° C. of 584 Pa·s.

Incozol 2 (from Incorez): 3-Butyl-2-(3-heptyl)-1,3-oxazolidine, based on N-butylethanolamine and 2-ethylhexanal, having a calculated oxazolidine equivalent weight of 227.4 g/eq.

The oxazolidines Ox-1 to Ox-4 are oxazolidines of the formula (I). The oxazolidines Ox-5, Ox-6 and Incozol 2 do not conform to the formula (I) and serve as a comparison.

Preparation of Polymers Containing Isocyanate Groups:
Polymer P1:

1300 g of polyoxypropylenediol (Acclaim® 4200, from Covestro; OH number 28.5 mg KOH/g), 2600 g of polyoxypropylenetriol (Caradol® MD34-02, from Shell; OH number 35.0 mg KOH/g), 600 g of diphenylmethane 4,4'-diisocyanate (Desmodur® 44 MC L, from Covestro) and 500 g of diisodecyl phthalate were reacted at 80° C. to give an NCO-terminated polyurethane polymer having a content of free isocyanate groups of 2.1% by weight.

Production of Polyurethane Compositions:
Compositions Z1 to Z14:

For each composition, the ingredients specified in tables 1 to 3 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture. Each composition was tested as follows:

As a measure of storage stability, viscosity was determined the day after production (1 d RT), and after storage for 7 days in a closed container at room temperature (7 d RT), and after storage for 7 days in a closed container in an air circulation oven at 60° C. (7 d 60° C.), as described above.

A measure determined for the open time was the skin time. For this purpose, a few grams of the composition were applied to cardboard in a layer thickness of about 2 mm and, under standard climatic conditions, the first period of time after which no residues remained any longer on an LDPE pipette used to gently tap the surface of the composition was determined.

For determination of mechanical properties, each composition was pressed between two wax-coated transfer printing papers to give a film of thickness 2 mm and stored under standard climatic conditions for 7 days. After the wax papers had been removed, some dumbbells having a length of 75 mm with a bar length of 30 mm and a bar width of 4 mm were punched out of the film, and these were tested to DIN EN 53504 at a strain rate of 200 mm/min for tensile strength (breaking force), elongation at break, modulus of elasticity 25% (at 0.5-25% elongation) and modulus of elasticity 100% (at 0.5-100% elongation).

Shore A hardness was determined according to DIN 53505 on test specimens cured under standard climatic conditions for 7 days.

The appearance of the test specimens produced for Shore hardness was assessed in relation to the presence of blisters and surface tack by tapping by finger. What is meant here by "tack-free" or "(tack-free)" is that the film was entirely or virtually without surface tack.

The results are reported in tables 1 to 3.

The compositions labeled "(Ref.)" are comparative examples.

The thickener was produced beforehand by gently heating an initial charge of 300 g of diisodecyl phthalate and 48 g of diphenylmethane 4,4'-diisocyanate (Desmodur® 44 MC L, from Covestro) in a vacuum mixer and then slowly adding 27 g of monobutylamine dropwise while stirring vigorously. The resultant paste was stirred for a further hour under reduced pressure while cooling.

Aldimine-1 was prepared by adding 13.93 g of 3-aminomethyl-3,5,5-trimethylcyclohexylamine (Vestamin® IPD, from Evonik Industries) to an initial charge of 50.00 g of 2,2-dimethyl-3-lauroyloxypropanal in a round-bottom flask under a nitrogen atmosphere while stirring, and then removing the volatile constituents at 80° C. and a reduced pressure of 10 mbar. A pale yellow odorless liquid having a viscosity of 0.2 Pa·s at 20° C. and an amine value of 153.0 mg KOH/g was obtained.

TABLE 1

Composition and properties of Z1 to Z6.

| Composition | Z1 (Ref.) | Z2 | Z3 | Z4 | Z5 | Z6 |
|---|---|---|---|---|---|---|
| Polymer P1 | 105.00 | 105.00 | 105.00 | 105.00 | 105.00 | 105.00 |
| Oxazolidine | — | 3.17 | 3.49 | 3.99 | 4.65 | 2.82 |
|  |  | Ox-1 | Ox-2 | Ox-3 | Ox-4 | Ox-3 |
| Thickener | 60.00 | 60.00 | 60.00 | 60.00 | 60.00 | 60.00 |
| Diisodecyl phthalate | 30.00 | 30.00 | 30.00 | 30.00 | 30.00 | 30.00 |
| Chalk[1] | 100.00 | 100.00 | 100.00 | 100.00 | 100.00 | 100.00 |
| Silica[2] | 7.00 | 7.00 | 7.00 | 7.00 | 7.00 | 7.00 |
| Salicylic acid solution[3] | 2.00 | 2.00 | 2.00 | 2.00 | 2.00 | 2.00 |
| DBTDL solution[4] | 1.00 | 1.00 | 1.00 | 1.00 | 1.00 | 1.00 |
| Ox/NCO ratio[5] | — | 0.37 | 0.37 | 0.37 | 0.37 | 0.26 |
| Viscosity (1 d RT) | 136 | 178 | 173 | 126 | 115 | 139 |
| at 20° C. (7 d RT) | 140 | 207 | 180 | 140 | 122 | 143 |
| [Pa·s] (7 d 60° C.) | 158 | 289 | 260 | 178 | 144 | 181 |
| Skin time | 90' | 70' | 85' | 130' | 130' | 100' |
| Tensile strength [MPa] | 2.3 | 2.9 | 2.0 | 2.2 | 1.3 | 2.5 |
| Elongation at break [%] | 400 | 900 | 975 | 990 | 935 | 870 |
| Modulus of elasticity 25% [MPa] | 3.3 | 1.4 | 1.2 | 1.0 | 0.9 | 1.8 |
| Modulus of elasticity 100% | 1.4 | 0.8 | 0.7 | 0.6 | 0.5 | 0.9 |
| Shore A | 52 | 36 | 29 | 32 | 28 | 37 |
| Appearance: |  |  |  |  |  |  |
| Blisters | many | none | none | none | none | none |
| Surface | tack-free | (tack-free) | (tack-free) | (tack-free) | (tack-free) | (tack-free) |

[1] Omyacarb® 5GU, from Omya
[2] Aerosil® R972, from Evonik Industries
[3] 5% by weight in dioctyl adipate
[4] 5% by weight of dibutyltin dilaurate in diisodecyl phthalate
[5] numerical ratio between oxazolidine groups and isocyanate groups in the composition

TABLE 2

Composition and properties of Z7 to Z11.

| Composition | Z7 | Z8 | Z9 | Z10 | Z11 |
|---|---|---|---|---|---|
| Polymer P1 | 105.00 | 105.00 | 105.00 | 105.00 | 105.00 |
| Oxazolidine | 2.04 | 1.13 | 1.24 | 1.42 | 1.66 |
|  | Ox-3 | Ox-1 | Ox-2 | Ox-3 | Ox-4 |
| Aldimine-1 | 7.13 | — | — | — | — |
| Thickener | 60.00 | 60.00 | 60.00 | 60.00 | 60.00 |
| Diisodecyl phthalate | 30.00 | 30.00 | 30.00 | 30.00 | 30.00 |
| Chalk[1] | 100.00 | 100.00 | 100.00 | 100.00 | 100.00 |
| Silica[1] | 7.00 | 7.00 | 7.00 | 7.00 | 7.00 |
| Salicylic acid solution[1] | 2.00 | 2.00 | 2.00 | 2.00 | 2.00 |
| DBTDL solution[4] | 1.00 | 1.00 | 1.00 | 1.00 | 1.00 |
| Ox/NCO ratio[1] | 0.19 | 0.13 | 0.13 | 0.13 | 0.13 |
| (Ox + Ald)/NCO ratio[2] | 0.56 | — | — | — | — |
| Viscosity (1 d RT) | 120 | 124 | 132 | 125 | 117 |

TABLE 2-continued

Composition and properties of Z7 to Z11.

| Composition | Z7 | Z8 | Z9 | Z10 | Z11 |
|---|---|---|---|---|---|
| at 20° C. (7 d RT) | 121 | 135 | 139 | 135 | 128 |
| [Pa · s] (7 d 60° C.) | 163 | 161 | 173 | 164 | 143 |
| Skin time | 40' | 105' | 110' | 105' | 105' |
| Tensile strength [MPa] | 2.4 | 2.2 | 2.0 | 2.0 | 2.2 |
| Elongation at break [%] | 905 | 510 | 455 | 480 | 618 |
| Modulus of elasticity 25% [MPa] | 1.8 | 2.5 | 2.4 | 2.6 | 2.3 |
| Modulus of elasticity 100% | 0.8 | 1.2 | 1.1 | 1.2 | 1.1 |
| Shore A | 34 | 45 | 43 | 47 | 47 |
| Appearance: | | | | | |
| Blisters | none | many | many | many | many |
| Surface | (tack-free) | tack-free | tack-free | tack-free | tack-free |

[1] as specified in table 1
[2] numerical ratio between the sum total of oxazolidine plus aldimine groups and isocyanate groups in the composition

TABLE 3

Composition and properties of Z12 to Z14.

| Composition | Z12 (Ref.) | Z13 (Ref.) | Z14 (Ref.) |
|---|---|---|---|
| Polymer P1 | 105.00 | 105.00 | 105.00 |
| Oxazolidine | 4.38 | 5.38 | 4.40 |
|  | Ox-5 [2] | Ox-6 [3] | Inc. 2 [4] |
| Thickener | 60.00 | 60.00 | 60.00 |
| Diisodecyl phthalate | 30.00 | 30.00 | 30.00 |
| Chalk[1] | 100.00 | 100.00 | 100.00 |
| Silica[1] | 7.00 | 7.00 | 7.00 |
| Salicylic acid solution[1] | 2.00 | 2.00 | 2.00 |
| DBTDL solution[1] | 1.00 | 1.00 | 1.00 |
| Ox/NCO ratio[1] | 0.37 | 0.37 | 0.37 |
| Viscosity (1 d RT) | 108 | 182 | 159 |
| at 20° C. (7 d RT) | 114 | 195 | 218 |
| [Pa · s] (7 d 60° C.) | 154 | 290 | 516 |
| Skin time | 145' | 30' | 80' |
| Tensile strength [MPa] | 1.9 | 2.1 | 2.0 |
| Elongation at break [%] | 460 | 190 | 880 |
| Modulus of elasticity 25% [MPa] | 2.6 | 3.2 | 1.4 |
| Modulus of elasticity 100% | 1.1 | 1.4 | 0.8 |
| Shore A | 50 | 51 | 35 |
| Appearance: | | | |
| Blisters | many | none | none |
| Surface | tack-free | tack-free | tack-free |

[1] as specified in table 1
[2] freshly prepared
[3] heated to 60° C.
[4] Incozol 2 (from Incorez)

The invention claimed is:

1. A polyurethane composition comprising at least one polymer containing isocyanate groups, obtained from the reaction of at least one polyol and at least one diisocyanate, and at least one oxazolidine of the formula (I)

$$\underset{R^2}{\overset{R^1}{\underset{|}{N}}}\underset{O}{\overset{}{\bigg\rangle}}G \quad (I)$$

where
R$^1$ is an alkyl or cycloalkyl or arylalkyl radical having 1 to 8 carbon atoms,
R$^2$ is H or methyl, and
G is an aromatic radical selected from the group consisting of furanyl, thiophenyl, pyridinyl, indenyl, indanyl, benzodioxolyl, benzodioxanyl, naphthyl, tetrahydronaphthyl, anthracenyl and a radical of the formula $$\text{----}\!\!\left\langle\!\!\!\bigcirc\!\!\!\right\rangle\!\!-\!(R^3)_n$$

where
R$^3$ is fluoro, chloro, bromo, nitro, cyano, phenyl, phenoxy, (C$_1$ to C$_5$)-alkyl or (C$_1$ to C$_5$)-alkoxy, and
n is 0, 1, 2 or 3.

2. The polyurethane composition as claimed in claim 1, wherein the polymer containing isocyanate groups has an NCO value in the range from 0.5% to 5% by weight.

3. The polyurethane composition as claimed in claim 1, wherein the diisocyanate is selected from the group consisting of hexamethylene 1,6-diisocyanate, perhydro(diphenylmethane 4,4'-diisocyanate), tolylene 2,4-diisocyanate or mixtures thereof with tolylene 2,6-diisocyanate, and diphenylmethane 4,4'-diisocyanate, optionally with fractions of diphenylmethane 2,4'- and/or 2,2'-diisocyanate.

4. The polyurethane composition as claimed in claim 1, wherein the polyol contains at least one triol.

5. The polyurethane composition as claimed in claim 1, wherein R$^1$ is methyl, ethyl, n-butyl or benzyl.

6. The polyurethane composition as claimed in claim 1, wherein G is furan-2-yl, 1,3-benzodioxol-5-yl, 1-naphthyl or a radical of the formula $$\text{----}\!\!\left\langle\!\!\!\bigcirc\!\!\!\right\rangle\!\!-\!(R^3)_n.$$

7. The polyurethane composition as claimed in claim 1, wherein G is phenyl, 2-methylphenyl, 3-methylphenyl, 4-methylphenyl, 4-isopropylphenyl or 4-methoxyphenyl.

8. The polyurethane composition as claimed in claim 1, wherein the numerical ratio between oxazolidine groups and isocyanate groups is in the range from 0.2 to 0.45.

9. The polyurethane composition as claimed in claim 1, wherein at least one aldimine of the formula $A\!-\![\!N\!\!=\!\!CHB]_y$ is additionally present, where y is 2 or 3, A is an organic radical having 2 to 25 carbon atoms, and B is an organic radical having 3 to 30 carbon atoms.

10. The polyurethane composition as claimed in claim 9, wherein the numerical ratio between oxazolidine groups and isocyanate groups is in the range from 0.1 to 0.3, and the numerical ratio between the sum total of oxazolidine plus aldimine groups and the isocyanate groups is in the range from 0.3 to 0.8.

11. The polyurethane composition as claimed in claim 1, wherein at least one further constituent selected from the group consisting of fillers, plasticizers, diisocyanate oligomers, catalysts and stabilizers is present.

12. The polyurethane composition as claimed in claim 1, wherein it is a one-component moisture-curing composition.

13. A method of bonding and/or sealing, comprising the steps of
 (i) applying the polyurethane composition as claimed in claim 1
  to a first substrate and contacting the composition with at least one second substrate within the open time of the composition, or
  to a first and to a second substrate and joining the two substrates within the open time of the composition, or
  between at least two substrates,
 (ii) curing the composition by contact with moisture.

14. A method of coating and/or sealing, comprising the steps of
 (i) applying the polyurethane composition as claimed in claim 1 to at least one substrate,
 (ii) curing the composition by contact with moisture.

15. An article obtained from a method as claimed in claim 13.

* * * * *